(12) United States Patent
Garden

(10) Patent No.: US 9,833,804 B2
(45) Date of Patent: Dec. 5, 2017

(54) NOZZLE APPARATUS

(71) Applicant: RIGDELUGE GLOBAL LIMITED, Aberdeen (GB)

(72) Inventor: Ian Garden, Alford (GB)

(73) Assignee: Rig Deluge Global Limited, Aberdeen (GB)

( * ) Notice: Subject to any disclaimer, the term of this patent is extended or adjusted under 35 U.S.C. 154(b) by 0 days.

(21) Appl. No.: 14/413,278

(22) PCT Filed: Jul. 9, 2013

(86) PCT No.: PCT/GB2013/051811
§ 371 (c)(1),
(2) Date: Jan. 7, 2015

(87) PCT Pub. No.: WO2014/009713
PCT Pub. Date: Jan. 16, 2014

(65) Prior Publication Data
US 2015/0190833 A1    Jul. 9, 2015

(30) Foreign Application Priority Data

Jul. 9, 2012  (GB) .................................... 1212199.2
Oct. 10, 2012  (GB) .................................... 1218133.5
May 13, 2013  (GB) .................................... 1308561.8

(51) Int. Cl.
*G01N 5/04*    (2006.01)
*B05B 15/00*    (2006.01)
(Continued)

(52) U.S. Cl.
CPC ............ *B05B 15/008* (2013.01); *A62C 31/02* (2013.01); *B05B 15/02* (2013.01); *B05B 15/065* (2013.01); *G01N 5/04* (2013.01); *Y10T 29/49432* (2015.01)

(58) Field of Classification Search
CPC .... Y10T 29/49432; G01N 5/04; A62C 31/02; B05B 15/008; B05B 15/02; B05B 15/065
See application file for complete search history.

(56) References Cited

U.S. PATENT DOCUMENTS 1,508,480 A    9/1924  Skinner
1,563,490 A    12/1925 Horton
(Continued)

FOREIGN PATENT DOCUMENTS

CA         492585 A      5/1953
CN       201524483      7/2010
(Continued)

OTHER PUBLICATIONS

Official International Search Report dated Jun. 11, 2013 from corresponding European Application No. GB1308561.8.
(Continued)

*Primary Examiner* — David Bolduc
(74) *Attorney, Agent, or Firm* — Willis IP; Ryan Willis

(57) ABSTRACT

A nozzle apparatus comprising: an inlet, an outlet, a filter disposed between the inlet and the outlet, and, a container; wherein the nozzle apparatus defines a first flow path for particles too large for said filter and a second flow path towards the outlet for particles small enough for said filter; and wherein the container is provided downstream of the first flow path. In this way the pressure on the container downstream of the first fluid path causes the debris to accumulate therein and the nozzle is less liable to blockages. The apparatus is of particular use as a sprinkler system.

19 Claims, 17 Drawing Sheets

(51) Int. Cl.
A62C 31/02 (2006.01)
B05B 15/06 (2006.01)
B05B 15/02 (2006.01)

(56) References Cited

U.S. PATENT DOCUMENTS

| | | | |
|---|---|---|---|
| 1,617,858 A | | 2/1927 | March |
| 2,493,982 A | | 1/1950 | Lee |
| 2,629,632 A | | 2/1953 | Munson |
| 3,268,176 A | | 8/1966 | O'Brien et al. |
| 4,064,046 A | | 12/1977 | Gilger |
| 4,848,672 A | | 7/1989 | Matsumoto et al. |
| 5,269,913 A | * | 12/1993 | Atkins .................. B01D 29/23 15/1.7 |
| 5,863,443 A | * | 1/1999 | Mainwaring ...... B01D 21/0012 210/248 |
| 2002/0040868 A1 | | 4/2002 | Lockwood |
| 2002/0096580 A1 | | 7/2002 | Pahila |
| 2003/0052199 A1 | | 3/2003 | Ikeuchi et al. |
| 2004/0195362 A1 | | 10/2004 | Walker |
| 2004/0255377 A1 | | 12/2004 | Mueller et al. |
| 2008/0290197 A1 | | 11/2008 | Fecht et al. |
| 2009/0272826 A1 | | 11/2009 | Kioi |
| 2009/0294341 A1 | | 12/2009 | Beer et al. |
| 2011/0110811 A1 | | 5/2011 | Fecht et al. |
| 2012/0125867 A1 | | 5/2012 | Andersen |

FOREIGN PATENT DOCUMENTS

| | | |
|---|---|---|
| CN | 202667021 U | 1/2013 |
| CN | 201380046348 | 5/2015 |
| DE | 3741677 | 5/1989 |
| DE | 20301377 | 5/2003 |
| FR | 2229211 | 12/1974 |
| GB | 2142105 A | 1/1985 |
| GB | 2433710 A | 7/2007 |
| GB | 2441058 A | 2/2008 |
| GB | 2458740 A | 10/2009 |
| GB | 1212199.2 | 10/2012 |
| GB | 1308561.8 | 6/2013 |
| GB | 1407584.0 | 10/2014 |
| WO | 2005/084815 A2 | 9/2005 |
| WO | GB2013/051811 | 11/2013 |
| WO | GB2013/051812 | 12/2013 |

OTHER PUBLICATIONS

Official WIPO International Search Report dated Dec. 19, 2013 from corresponding PCT Application No. PCT/GB2013/051811.
Official International Search Report dated Oct. 17, 2012 from corresponding European Application No. GB1212199.2.

* cited by examiner

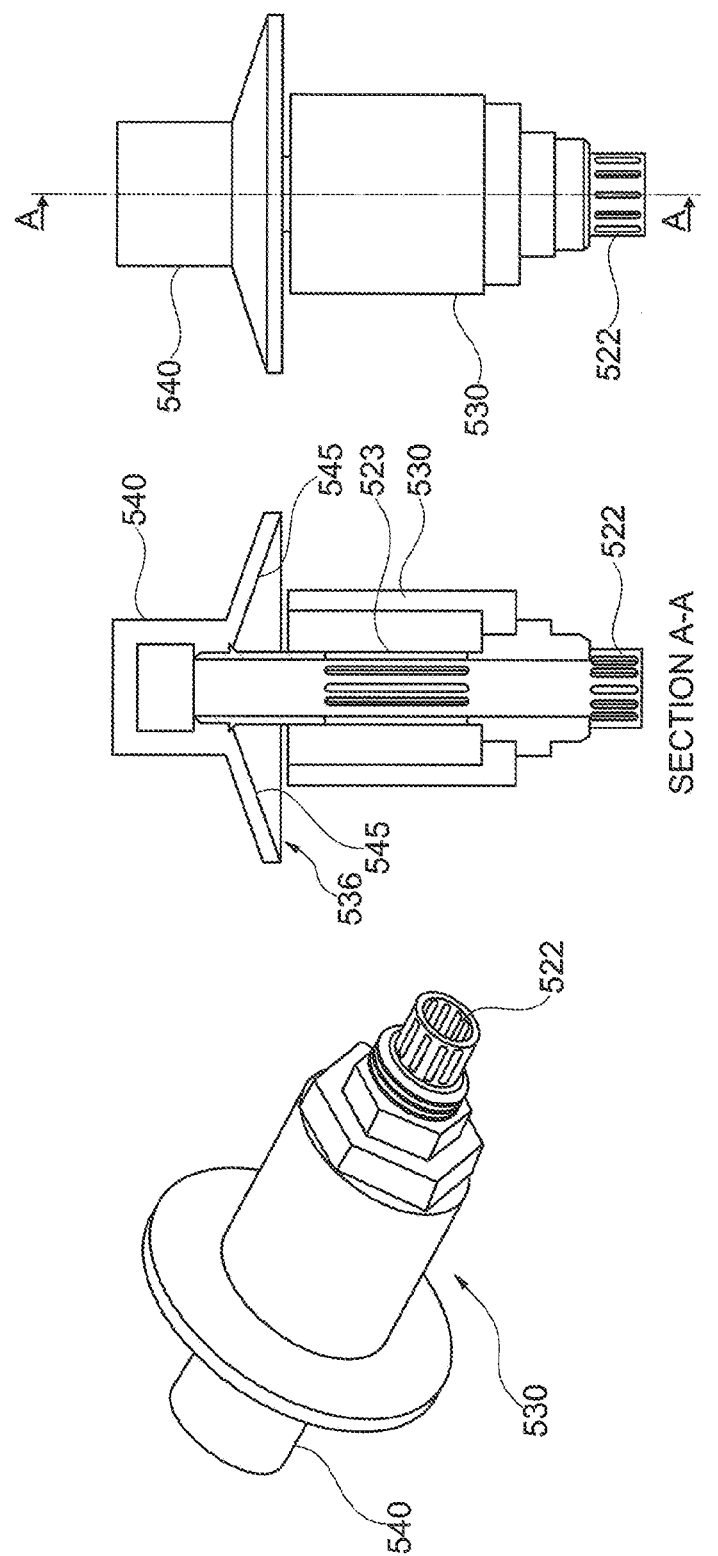

NOZZLE APPARATUS

This invention relates to a nozzle apparatus for distributing fluid and a nozzle system comprising the nozzle apparatus a pipeline.

Nozzle apparatus or sprinklers are widely used in buildings and other installations, such as offshore oil and gas platforms. When operating an open sprinkler system scale is inevitably present—it is built up by the oxidisation of metal by air and water. It is a regular occurrence for sprinkler nozzles to block and become redundant because of this scale or other pollutants.

Oil and gas burners have similar problems. Indeed, any fluid system that requires clear fluid path from an exit can be inhibited from pollutants of various kinds.

Traditional means to tackle the presence of scale or other particles which can potentially block the nozzle, include an upstream screen where larger particles are blocked. However the inventor of the present invention has recognised that this is still unsatisfactory partly because the screens themselves become blocked and inhibit or prevent fluid coming through the exit point of the fluid system, such as a sprinkler.

According to the present invention there is provided a nozzle apparatus comprising:
an inlet,
an outlet,
a filter disposed between the inlet and the outlet, and,
a container;
wherein the nozzle apparatus defines a first flow path for particles too large for said filter and a second flow path towards the outlet for particles small enough for said filter;
and wherein the container is provided downstream of the first flow path.

The filter is normally a screen comprising at least one aperture therein. Thus the first flow path is defined for particles too large for said aperture and the second flow path is defined for particles small enough to travel through said aperture.

Normally the nozzle apparatus comprises a removable portion to allow access to the container. This may be provided by the container itself, or part thereof, being removable.

The container is normally at least 2 cm$^3$ optionally more than 5 cm$^3$ optionally more than 10 cm$^3$. Normally the container is integral with the rest of the nozzle apparatus.

Typically the first and second flow paths start at the filter.

The inventor of the present invention has noted that debris tends to accumulate to an endpoint in a line. Preferably therefore the first flow path terminates in (or alternatively above) the container.

Thus aside from its direct fluid connection with the first flow path, preferably the container has no further direct (i.e. not through the first flow path) fluid communication with any other flow path of the nozzle apparatus. In use, the first flow path between the filter and the container is under pressure and so typically the only flow in the first flow path (after starting the flow through the overall nozzle apparatus) is a flow of suspended particles too large for said filter.

The apparatus may be arranged such that in use, fluid flow is directed onto an outer face of the container. The container may be appropriately shaped, for example have slots radially spaced around the edge thereof, optionally extending about 10-20 mm towards the centre of the container. The slots may be parallel with the direction of the fluid flow immediately before it contacts the container. Alternatively or additionally they may be generally vertical (+/−20 degrees) based on the orientation of the apparatus in use.

The removable portion is most normally a portion which can readily be reattached to the nozzle. Thus the removable portion may be removable by way of any one or more of a threaded connection, a snap fit connection, springs, clips, bolt & screw or others such mechanisms.

The removable portion may be the container, which may be connected as described herein (for example threadably connected) with another portion of the nozzle apparatus, such as the filter.

A passage defined between the filter and the container is normally larger than said at least one filter aperture.

Moreover, the container is normally in more direct fluid-communication with the inlet side of the filter compared to the outlet side of the filter.

The aperture is preferably linear in shape—one dimension is larger than a second dimension, with the third dimension being defined as the depth of the aperture. For example the first dimension may be more than 3, or more than 8, times the length of the second dimension.

The longer dimension may be parallel to the flow of fluid in use but depending on exit position certain embodiments may not be parallel. For example they may be perpendicular.

The screen is normally a tubular screen with a passage therein, and said at least one aperture thereon is on a face (rather than an end) of the tubular screen. Thus the second flowpath may be from/to the passage of the tubular screen to/from the outside of the tubular screen; preferably from the passage of the tubular screen, to the outside of the tubular screen.

Normally there are a plurality of apertures in the screen, such as from 4 to 20, optionally from 8 to 16 but this can vary depending on the size of the nozzle. The portion of the nozzle apparatus between the inlet and the screen will be referred to as the "inlet flow path" and the portion of the nozzle apparatus between the screen and the outlet will be referred to as the "outlet flow path". The portion of the nozzle apparatus between the screen and the container will be referred to as the "container flow path".

The inlet flow path may be a relatively central portion of the nozzle compared to the outlet flow path although this depends on the actual water pattern required.

The inlet flow path and the first flow path are preferably co-linear and more preferably co-linear with the container flow path. The cross-sectional size of the inlet flow path is preferably the same size (optionally bigger) than the cross-sectional size of the first flow path and/or container flow path. These features allow certain embodiments to create a flow pressure to encourage the debris to accumulate in the end of the first flow path, which terminates in the container.

The outlet may be a channel, disposed at an angle of up to 179 degrees, optionally from 10 to 50 degrees.

An outer body may be provided, optionally to create a third flow path "the outlet flow path" between the filter and the outlet.

Preferably the size of the apertures in the first screen is equal to or smaller than the size of the outlet.

In this way, any particle small enough to travel through the apertures will not be likely to block the outlet since the outlet is the same size or larger.

For certain embodiments, an angled flange may be provided, preferably extending at least 300 degrees around the circumference of the apparatus, and at an angle of 5 to 90 degrees, often 60 to 85 degrees to the main longitudinal axis of the filter. The fluid may in use be directed onto the flange, and thereafter out of the apparatus. The flange may be attached to the debris pot and is preferably moulded as a one-piece with the debris pot.

The filter will hereinafter be referred to as the first filter.

The nozzle apparatus may further comprise an inlet filter, normally a screen comprising at least one first aperture, to resist flow of particles of a pre-defined size. Normally there is a plurality of first apertures. The shape and dimensions of the first apertures may include any optional feature described above with respect to the first screen described. In preferred embodiments, the length of the linear apertures is less than that of the apertures described further above for the first screen.

However, the inlet screen may comprise a second larger aperture (normally at its end) which is sized to allow the flow of such particles. This counter intuitive feature prevents blockage of the inlet screen should sufficient particles build up on the first aperture(s) (normally at the side thereof). Normally said second larger aperture therefore is preferably the same size (optionally bigger) than the size of the inlet flow path and the container flow path.

Preferably the size of the first apertures in the inlet screen are equal to or smaller than the size of the outlet.

The distance between the outer body and the screen normally affects the exit velocity of fluid in use. Normally said distance is in the range of 1-12 mm; therefore there is a channel of 1-12 mm between the screen and the outer body. Preferably for low velocity nozzle apparatus, the distance (width of channel) is in the range of 7-12 mm. For high velocity nozzles the distance (width of the channel) may be 2-5 mm or 2-3 mm.

For embodiments where a housing or outer body surrounds the container, this factor normally predominantly determines the exit velocity of the fluid in use.

For other embodiments, the spacing of the container from the outlet can also be varied in order to vary the exit velocity; especially for embodiments where the outer face of the container distributes the fluid. For example, if the container is spaced further away from the fluid outlet, then such a nozzle apparatus will tend to function as a lower velocity nozzle apparatus, for example since the fluid has had more time to depressurise before being distributed by the outer face of the container.

Typically there may be a space of 1-50 mm between the outlet and the container. For nozzle apparatus intended to be used as a low velocity nozzle, the distance is normally in the range of 10 mm to 30 mm. For nozzle apparatus intended to be used as a high velocity nozzle, the distance is normally in the range of 1 mm to 7 mm.

For example in one embodiment, the screen has 24×1 mm slots—and a 2-3 mm channel space between the screen and the outer body, and a 2 mm gap between outlet and the container.

The nozzles described herein may be attached to a pipeline such that there is fluid communication therebetween, and the nozzle's inlet extends into the pipeline such that at least a portion thereof is in the centre of the pipeline.

According to a second aspect of the invention, there is provided a nozzle system comprising a nozzle apparatus and a pipeline, the nozzle apparatus attached to the pipeline such that there is fluid communication therebetween, the nozzle apparatus having an inlet and an outlet, wherein the nozzle apparatus extends into the pipeline such that at least a portion of the inlet is in the centre of the pipeline.

The centre of the pipeline is within 15% of the central axis of the pipeline, measured by diameter. For example, in a 10 cm diameter pipeline which has a central axis at the midway point of the diameter, that is 5 cm, the centre is defined by the diameter +/−1.5 cm from the central axis with a total diameter of 3 cm.

Thus the inventor has noted that the conventional practise of placing a nozzle apparatus in the pipeline has drawbacks in that the pipe may block from time to time. However, by placing the inlet of the nozzle apparatus in the centre of the pipeline, debris that builds up in use on the inner edge of the pipeline will not block the nozzle apparatus, until the debris is particularly bad, such that it extends into the centre of the pipeline itself, which would probably block the pipeline itself. Accordingly such nozzles are an improvement over existing nozzles which are prone to blocking when some debris is present on the inner edge of a pipeline.

Generally, greater advantage is gained the closer the nozzle apparatus inlet is provided to the central axis of the pipeline. Accordingly the inlet may be within 10%, optionally 5% of the central axis of the pipeline.

The nozzle apparatus is normally attached to the pipeline at right angles, but can be at an angle of 60-100 degrees, or even larger, such as 20-160 degrees.

A portion of the nozzle apparatus inlet may be off-centre. For example a first inlet portion of the nozzle inlet is in the centre of the pipeline as described herein, and a second inlet portion, between the first inlet portion and the remainder of the nozzle apparatus, may be provided off centre and within the pipeline.

The remainder of the nozzle apparatus may comprise a filter.

The nozzle apparatus may be any nozzle apparatus described herein, optionally but not essentially, one also in accordance with the first aspect of the invention. Preferred and other optional features of the nozzle apparatus of the first aspect of the invention are preferred and optional aspects of the nozzle apparatus according to the second aspect of the invention.

In one embodiment known nozzles are converted to a nozzle apparatus according to the second aspect of the invention by adding an extension/adaptor piece so that the extended nozzle inlet extends into the pipeline such that at least a portion of the inlet of the extended nozzle is in the centre of the pipeline.

Thus the invention provides a method of modifying a nozzle, comprising adding an extension piece to a nozzle, such that the inlet of the nozzle with the extension piece extend into the centre of a pipeline. Such a method may be used with nozzle apparatus as described herein or conventional nozzles.

The extension piece may have a filter therein. The filter of the extension piece may have the same configuration as the filter/first filter described herein, and optional features of the filter/first filter are, independently, optional features of the filter of the extension piece.

The order of adding the extension piece to a nozzle apparatus can be varied. For example in one particular embodiment, the extension piece is first placed in a hole in the pipe, the extension piece extending into the centre of the pipe at one end, and then the nozzle is added to the extension piece at its other end. For example it may be secured inside by any suitable means such as by a thread.

The apparatus may be adapted to function with a water system, oil system (e.g. in oil burners) or any other fluid.

Fluid comprises liquid with or without gas. For example in the case of an oil burner, an oil/air mixture may be used.

The invention also provides a method of monitoring pipework integrity comprising weighing debris recovered from the pipework, and assessing the integrity of the pipework based on the weight of the debris.

This method is preferably performed using the apparatus described herein. It may be repeated over a period of time. Clearly the debris is indicative of a decaying pipework, and remedial action can be taken when assessing the pipework integrity, such as adding more chemical inhibitor, or replacing the pipework.

Embodiments of the present invention will now be described, by way of example only, with reference to the accompanying figures, in which:

FIG. 14a is a perspective view of a further embodiment of a nozzle apparatus in accordance with the present invention;

FIG. 14b is a side view of the FIG. 14a nozzle apparatus;

FIG. 14c is a sectional view through A-A of the FIG. 14b nozzle apparatus;

Figure 1:
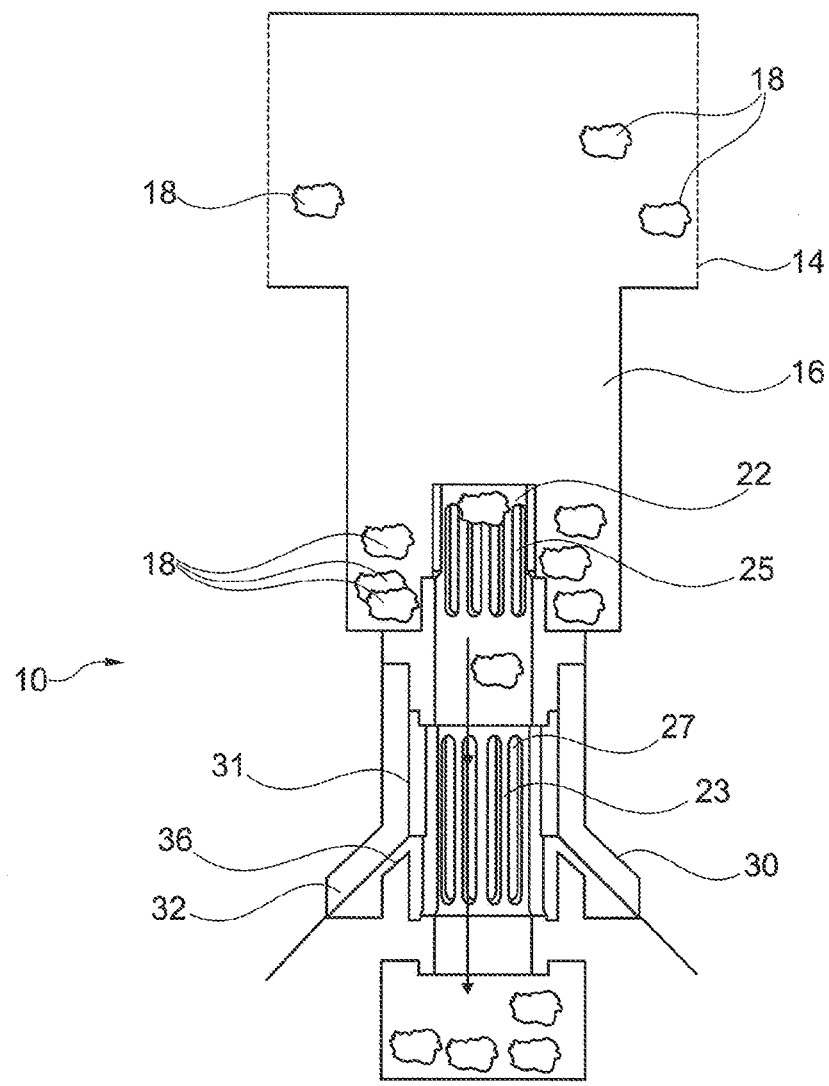
FIG. 1 is a cross-sectional view of a nozzle apparatus in accordance with the present invention in use.
Figure 2:
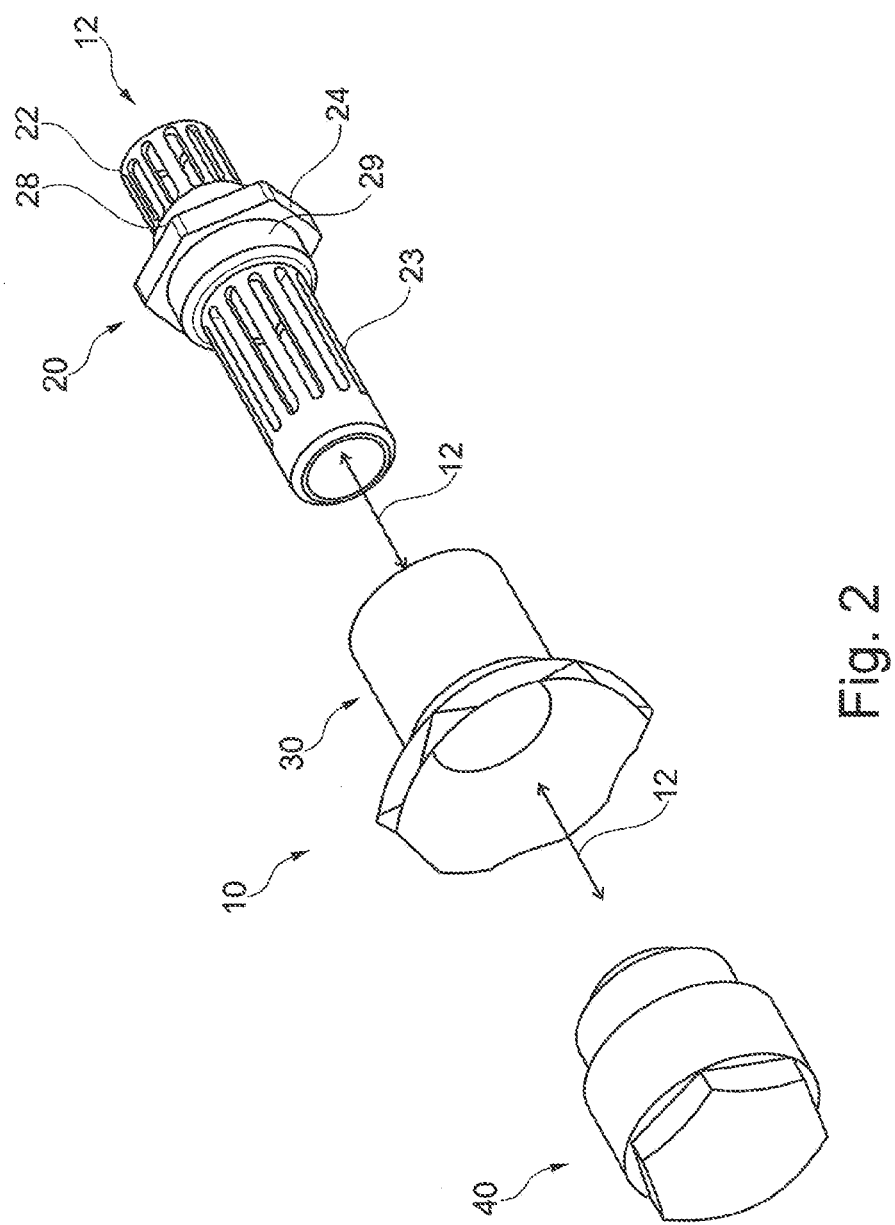
FIG. 2 is an exploded perspective view of the nozzle apparatus in accordance with the present invention.
Figure 3:
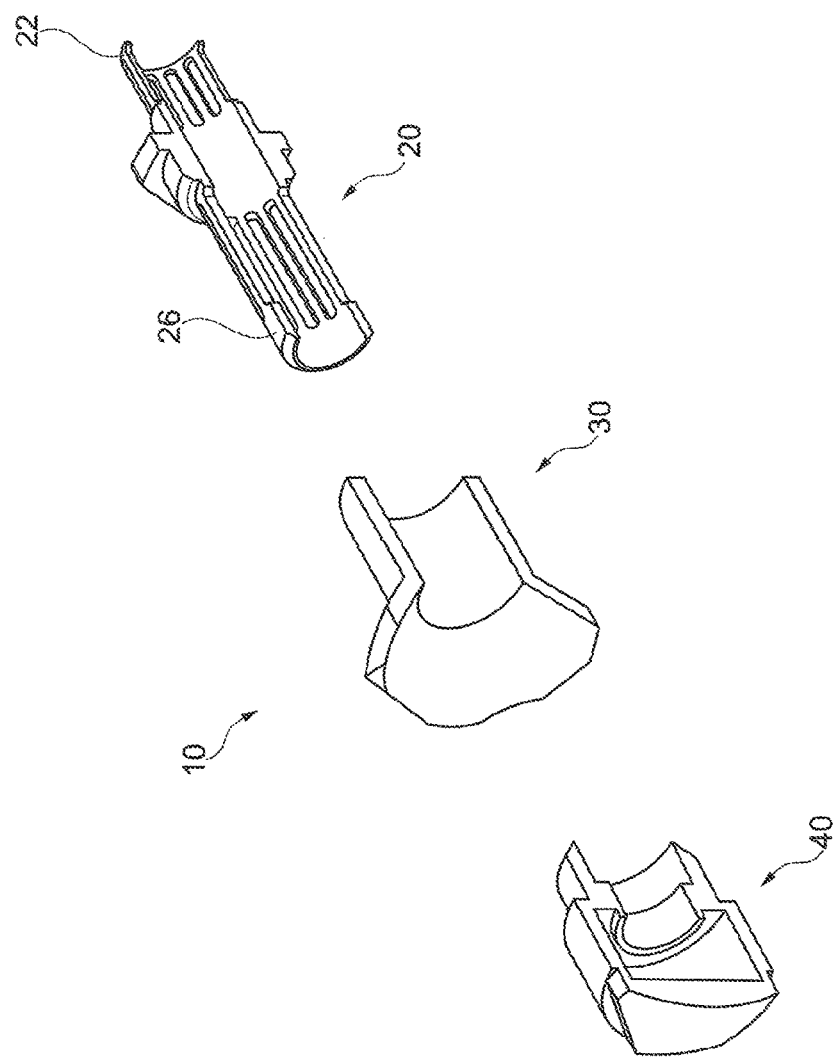
FIG. 3 is a cut-away exploded perspective view of the nozzle apparatus of FIG. 1.

FIGS. 1 and 2 show an embodiment of a nozzle apparatus 10 of the present invention comprising a screen apparatus 20 (comprising an entry segregator 22 and a main screen 23), an outer body 30 and a debris pot 40. Whilst this embodiment relates to water flow for use with a sprinkler, it will be appreciated that other fluids for different purposes could also be used with such a nozzle apparatus 10 or other nozzle apparatus in accordance with the present invention.

The various components 20, 30, 40; described in more detail below, fit together along their central axis so that, as shown in FIG. 1, the nozzle apparatus 10 may be attached to a T-piece 16 of a water pipe 14 or any fluid delivery system exit.

In use, the water pipe 14 contains water polluted by particulate debris 18. For the basic function, polluted water flows through a central passage 12 of the nozzle apparatus 10 and the water continues through the main screen 23 and through an outlet or exit channel 36 which directs it to the surrounding area. The particulate debris 18 which is too large to flow through the main screen 23, is directed to the container referred to as a debris pot 40. Thus the debris remains out of the way of the main screen 23 which prevents blockage of the screen 23 or blockage of the exit channel 36, thus allowing the nozzle apparatus 10 to function properly.

The debris pot 40 may be removed and replaced periodically to remove accumulated debris, which can be weighed to calculate corrosion rate as described below.

The different components of the nozzle apparatus 10 will now be described in more detail.

Figure 4:
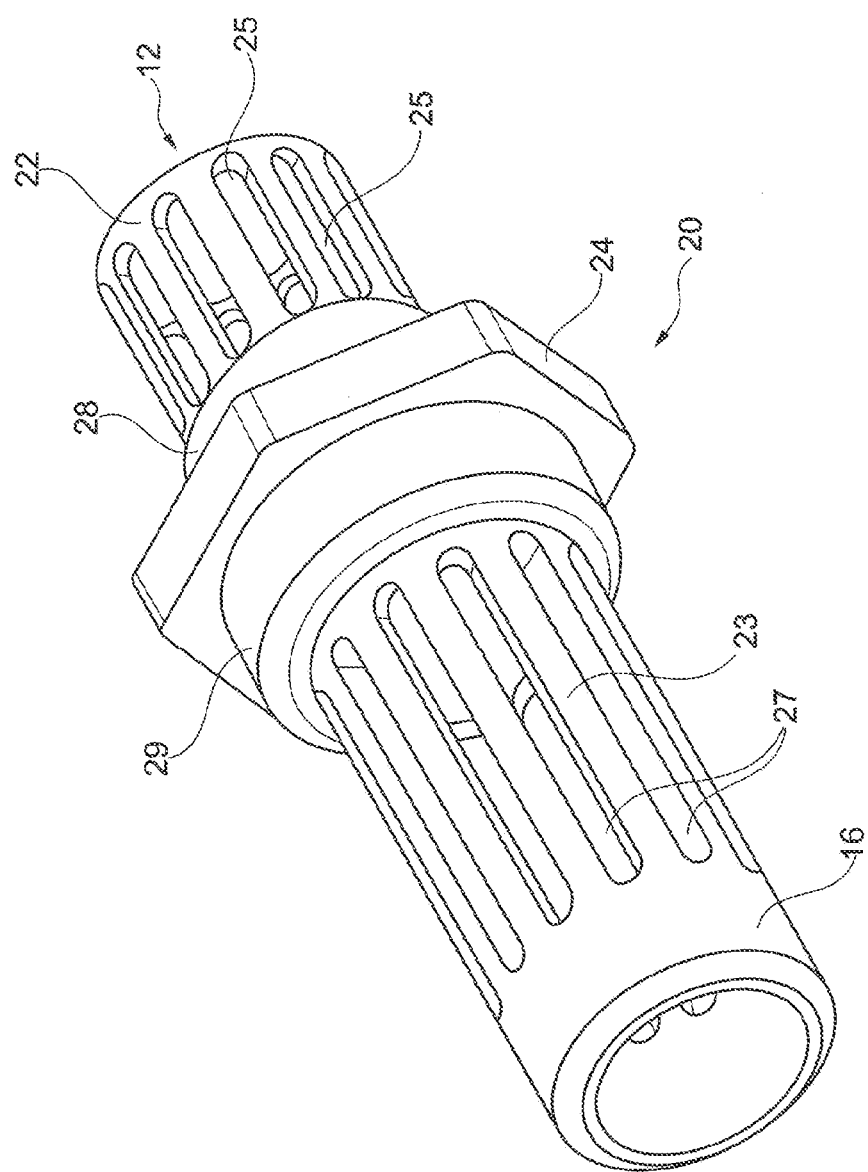
FIG. 4 is an enlarged perspective view of the screen apparatus of FIG. 1.
Figure 5:
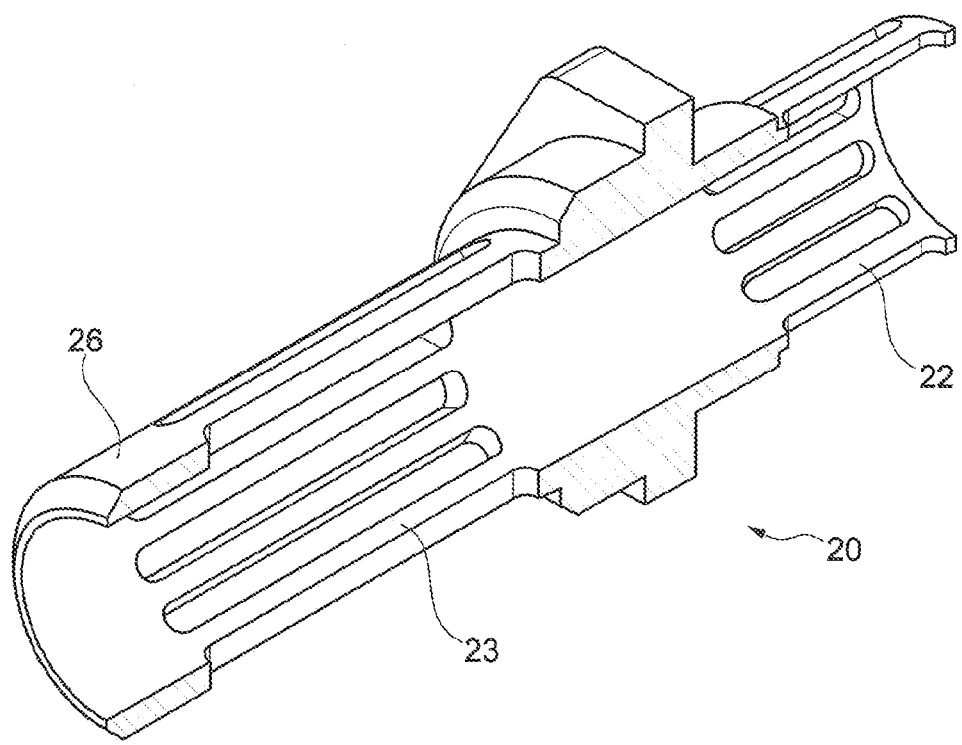
FIG. 5 is an enlarged cut-away perspective view of the screen apparatus of FIG. 1.

The screen apparatus 20, shown in more detail in FIGS. 4 and 5, comprises an entry segregator 22 which comprises a series of linear slots 25, which allow water and smaller particles to travel therethrough, but which block the passage of larger particles. The main screen 23 comprises a similar series of slots 27 (although typically somewhat longer) which separates the polluted water into (i) a debris enriched stream and (ii) a purer water stream. The entry segregator 22 and main screen 23 are mounted in axial alignment on either side of a hexagonal nut 24. The passage 12 extends through the entry segregator 22, nut 24 and main screen 23. A portion of the nut 24 extends radially outward from the entry segregator 22 and main screen 23, to provide a mounting for threads 28, 29 above and below, as described herein below.

The entry segregator 22 provides additional capacity to the filtration capacity of the nozzle apparatus 10, since debris may accumulate between the edge of the T-piece 16 and the entry segregator 22. The axial passage 12 (which is a larger aperture than the linear slots 20) is provided in the entry segregator 22 through which water as well as particles of various sizes can flow. Notably however, the passage 12 is large enough to receive the larger particles which cannot travel through the slots 25 in the entry segregator 22. Thus if the debris 18 builds up in this position, it will not block water flow and so not block the overall nozzle apparatus 10. Thus when the debris reaches its saturation point it will begin to flow over the entry segregator 22 into the passage 12. The entry segregator 22 is particularly suitable for vertical positioned nozzles.

The purer water stream travels through the slots 27 in the main screen 23 and out of the exit channel 36 and is directed by the outer body 30 to the surrounding area.

Figure 6:
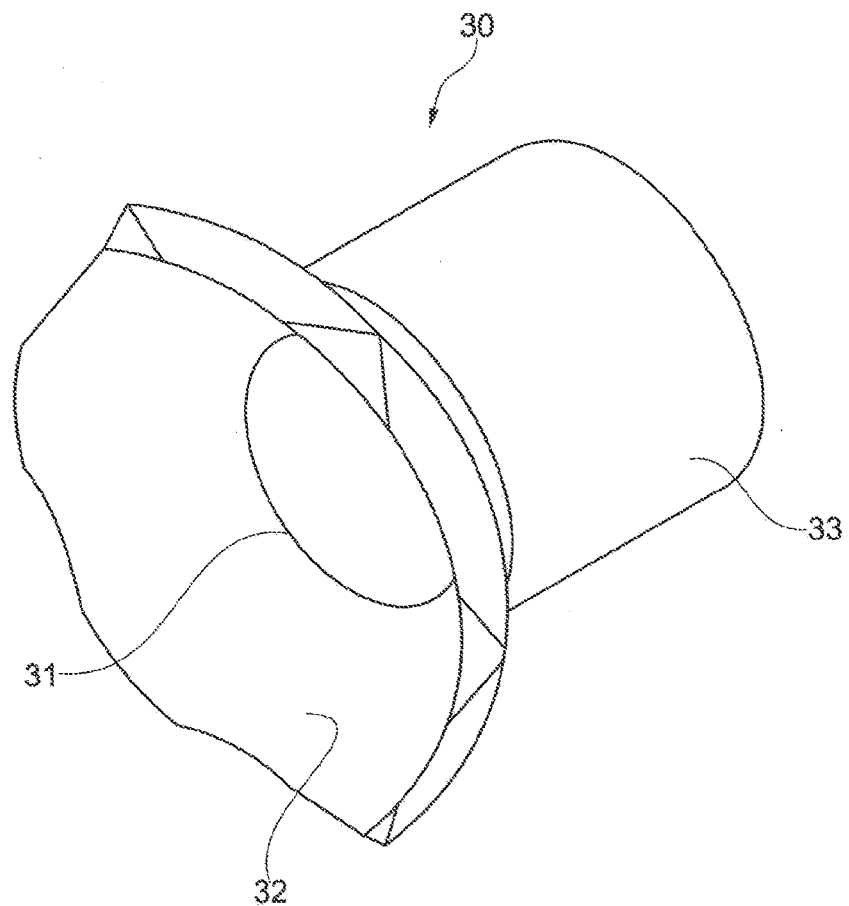
FIG. 6 is an enlarged perspective view of the nozzle of FIG. 1.

A larger view of the outer body 30 is shown in FIG. 6. It comprises an angled portion 32 the inner part 31 of which, along with a matching portion on a tube 48, is shaped to direct the water flow to the desired area. The angled portion 32 extends radially outwards compared to the opposite tube 48 but this does not further assist in directing the flow of water. Rather, it provides a larger gripping surface and has a hex profile to allow the tightening it to the main screen 23 for ease of assembly. The body 30 also includes a cover portion 33 which defines a flowpath between its inner bore and the main screen 23. The outer body 30 may be replaced by a variety of different bodies of varying sizes and different angles 31 in order to be properly sized for its intended purpose. In this embodiment, the outer body 30 provides a hollow cone spray at a 45 degree angle.

Figure 7:
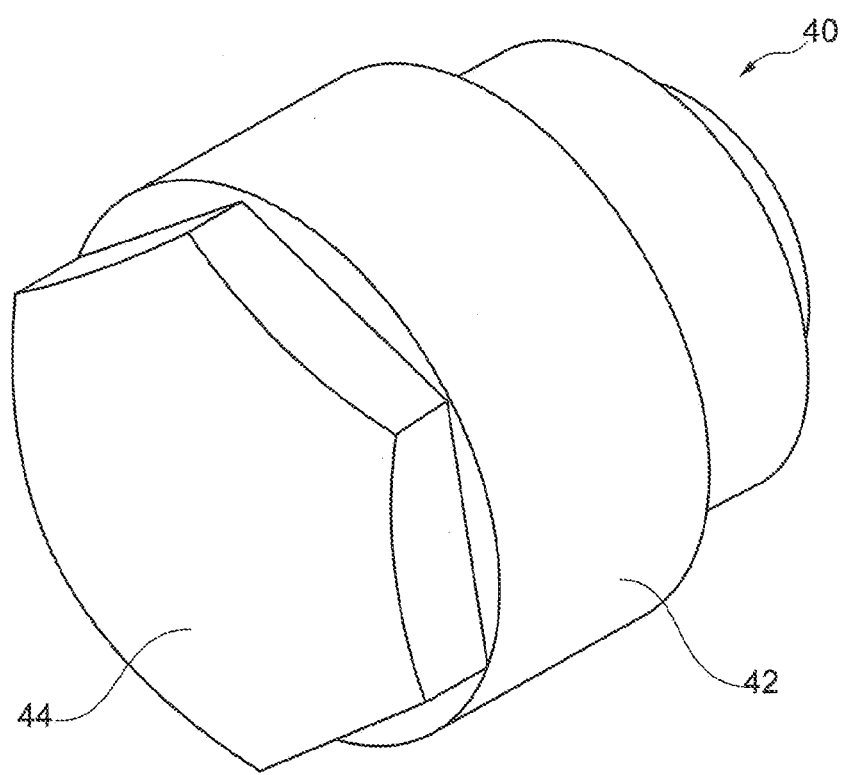
FIG. 7 is an enlarged perspective view of the debris pot of FIG. 1.
Figure 8:
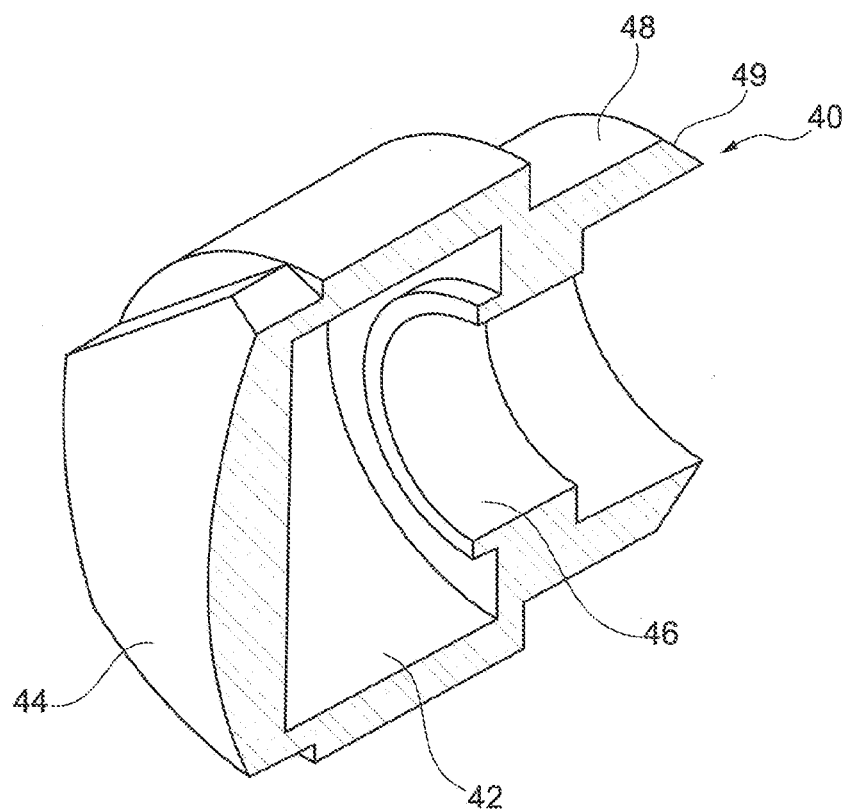
FIG. 8 is an enlarged cut-away perspective view of the nozzle of FIG. 1.

The debris pot 40 is shown in more detail in FIGS. 7 and 8 and comprises a container 42 with an end plate 44. At the open end of the debris pot, a socket 46 is threaded to receive a thread 26 on the end of the main screen 23 and a larger diameter (than the socket) tube portion 48 extends from the container 42 further in the axial direction.

To assemble the nozzle apparatus 10 for first-use, the screen apparatus 20 is affixed to the T-piece 5 via a thread 28 mounted on the nut flange 24. The entry segregator 22 thus extends up into the T-piece 5 or other pipework to which it is fitted and the main screen 23 extends from the opposite side of the nut 24 (normally in a downwards direction). The cover portion of the outer body 30 is then placed over the and around the main screen 23 and is affixed to the thread 29. Finally, the socket 46 in the debris pot 40 is attached to a thread 26 at the end of the main screen 23. The edge 49 of the tube portion 48 is then aligned with and spaced slightly away from the inner end 31 of the outer body 30 and the resulting gap 18 (shown in FIG. 1) between them provides the exit channel 36 for the water. Notably the edge 49 is angled to reflect the angle of the inlet end 31 of the outer body 30 (thus providing an angled channel), both of which may be varied depending on the desired coverage or other factors.

For the debris particles that are too large to proceed through the slots 21, they proceed to the debris pot 40. The container 42 is sized to allow a large volume of debris to be trapped under pressure.

Thus embodiments of the present invention provide a debris free environment allowing water to pass through the nozzles ensuring it achieves the required K-Factor for its optimum performance.

Embodiments of the present invention benefit in that to completely block the nozzle it will take very large amounts of scale and debris without maintenance from clearing out the debris pots unlike many existing solutions that will almost instantly fail.

Indeed for certain embodiments of the invention there are twelve slots in the main screen 23 but the nozzle can still deliver the volume and pressure of water required by the nozzle for its optimum performance if only two of these slots are free from debris.

The exit channel 36 can be set at any angle. The angle on this example is 45 degrees, this is specific for cooling operations as it sends water forward at its optimal angle to reach its furthest point away from the structure it is protecting. This angle is matched by tube 48 of the debris pot 40 to form the exit channel 36. Preferably the debris pot 40 is no larger than the outer body 32.

The main screen 23 and the cover 33 are sized to optimise the correct water volume and pressure through to the exit channel 36.

The first embodiment is shown attached to a T-piece but the nozzle apparatus can easily attach to any fluid transfer exit—an exit point vertical facing up or down—horizontal etc. could also be used.

Figure 9:
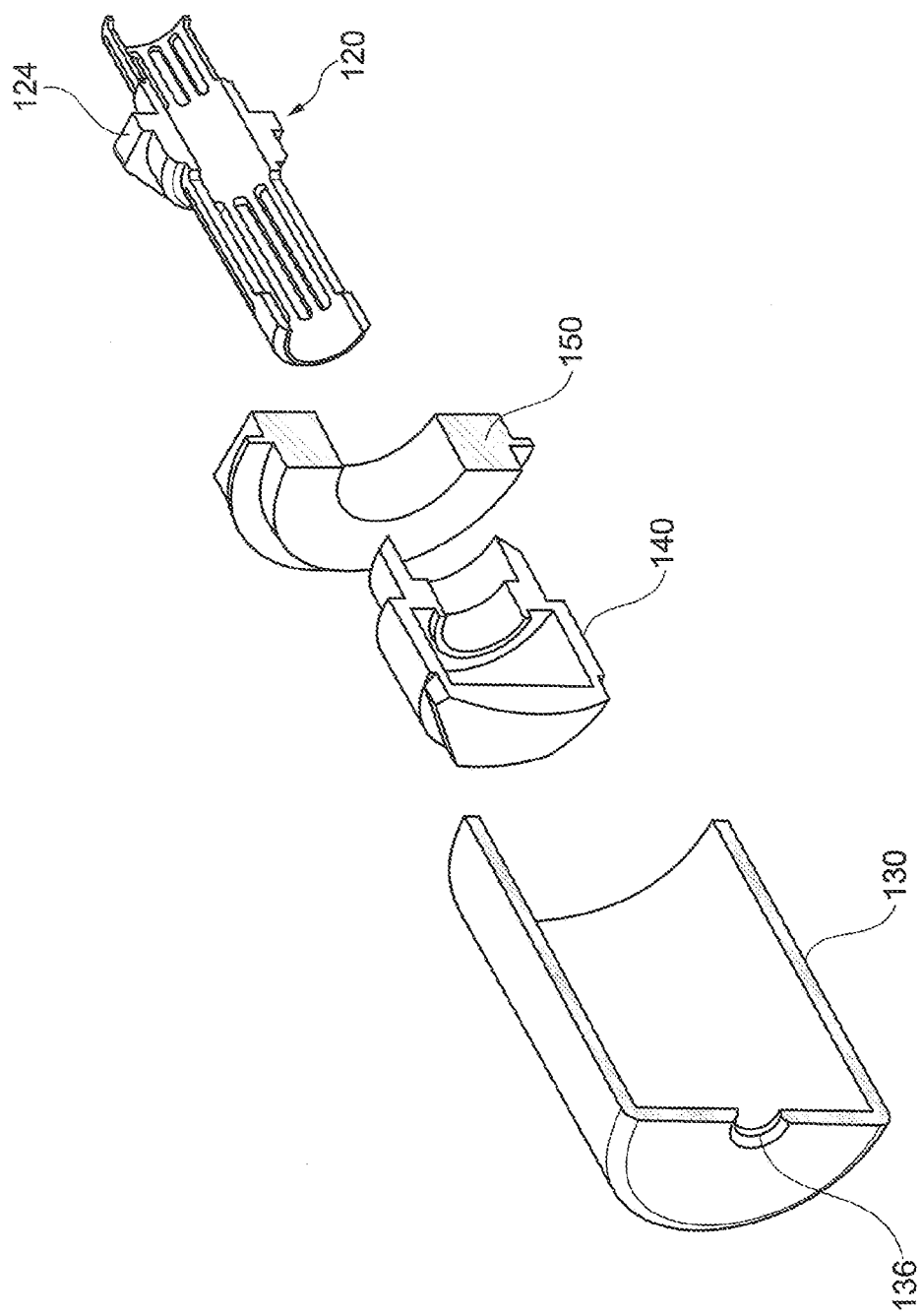
FIG. 9 is a cut-away exploded perspective view of a second embodiment of a nozzle apparatus according to the present invention.

FIG. 9 shows a second embodiment of a nozzle apparatus 110 of the present invention; like parts share the same reference numeral except preceded by a '1'. The nozzle apparatus 110 comprises a screen apparatus 120, an outer body 130 and a debris pot 140.

The screen apparatus 120 and debris pot 140 function as described for the earlier embodiment, and will not be described further.

In this embodiment however, the outer body 130 is a cylindrical shape with one end open and the opposite end having an exit channel 136. The outer body 130 encloses the debris trap 140, and is secured against a support member 150, which in turn is secured to a circumferentially extending nut 124 on the screen apparatus 120.

Figure 10:
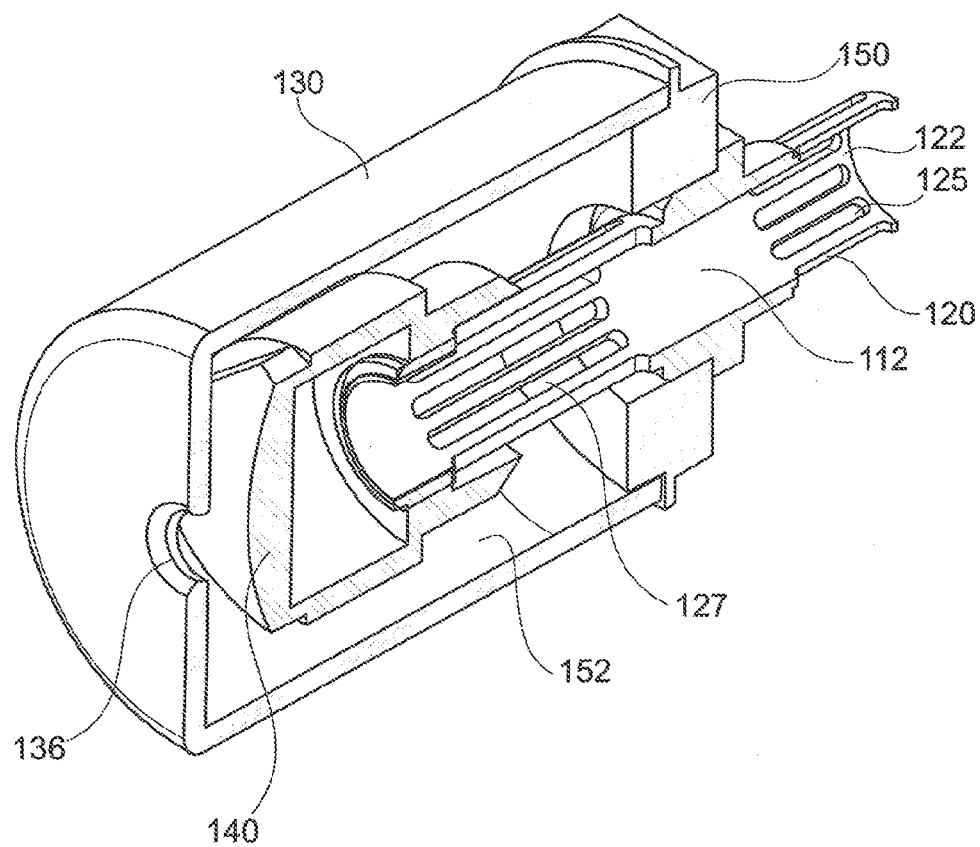
FIG. 10 is a cut-away perspective view of the assembled FIG. 9 embodiment.

The assembled nozzle apparatus 110 is shown in FIG. 10. In use, the water (or other fluid), enters the nozzle apparatus through an entry segregator 122, which impedes the flow of debris particles through its smaller slots 125. The flow continues through the central passage 112 of the screen apparatus 120, through the slots 127 in the main screen 123 and then into a void 152 between the outer body 130 and debris pot 140/main screen 123. Particulate debris too large to proceed through the slots 127 reside in the debris pot 140. The water flow continues out of the exit channel 136, which can be suitably sized for the desired application, for example creating a mist. This arrangement allows a full cone spray profile.

An advantage of certain embodiments of the invention is that the screens are provided in the nozzle apparatus close to the exit channel. Therefore, pollutants (such as scale coming off pipework) are caught from the pipework. This contrasts to other designs where a screen or filter is provided upstream in the pipework and any scale released downstream of the screen is not screened out and so may block the nozzles.

Figure 11:
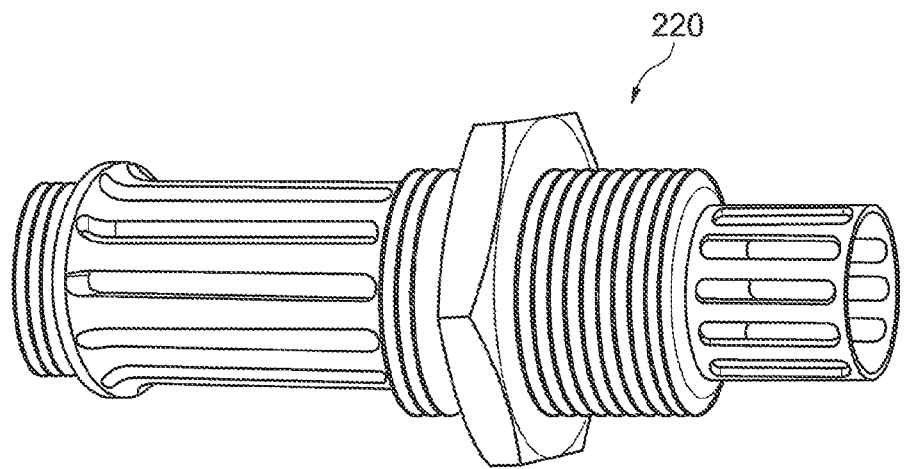
FIG. 11 is a perspective view of one embodiment of a filter apparatus of the present invention.
Figure 12:
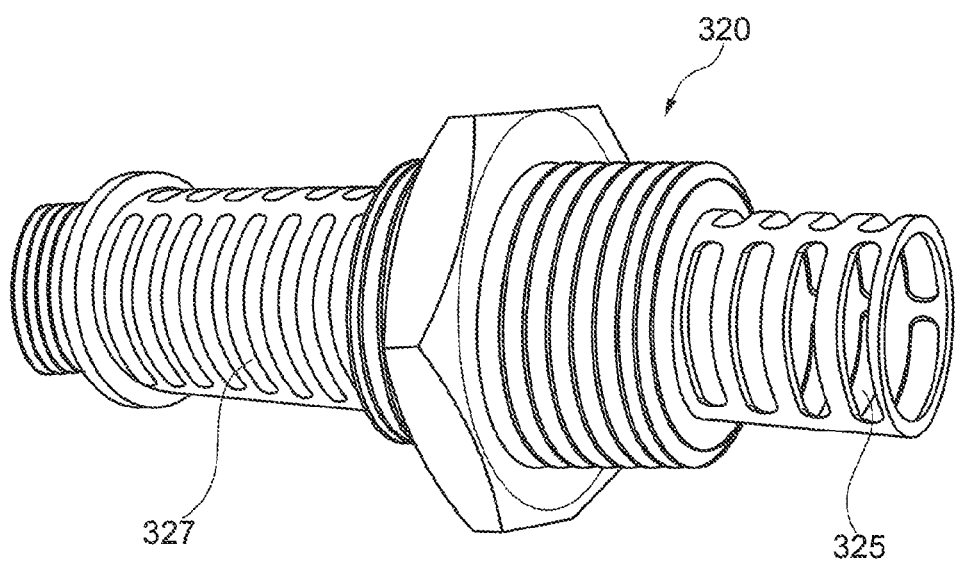
FIG. 12 is a perspective view of one embodiment of an alternative filter apparatus of the present invention.

Some alternative screen apparatus 220, 320 is shown in FIGS. 11 and 12 and these function in a similar manner as the earlier embodiments. In FIG. 12 it can be seen that the slots 325, 327 are arranged in a perpendicular direction to the flow of fluid in contrast to the earlier embodiments.

In any case, the arrangement of the slots for preferred embodiments of the invention, is configured such that the length of the outer body and the passage through the screen allow enough volume through to the outlet even if 80% of the screen is blocked. The provision of slots rather than small circular hole screens, facilitates such an effect, which also minimises pressure build up on the screen and lost pressure from the expelled fluid.

Not only do embodiments of the present invention allow storage of debris but it can also be used to determine the rate of corrosion within the deluge line. After every function test of the system all the debris pots can be removed with the debris being stored for weighing. The weight and volume of the debris can be calculated to show corrosion rate when referenced with the frequency of the test. This feature will allow the operator to evaluate the life of the whole system and determine when it requires a full re-structure and re-placement.

Figure 13B:
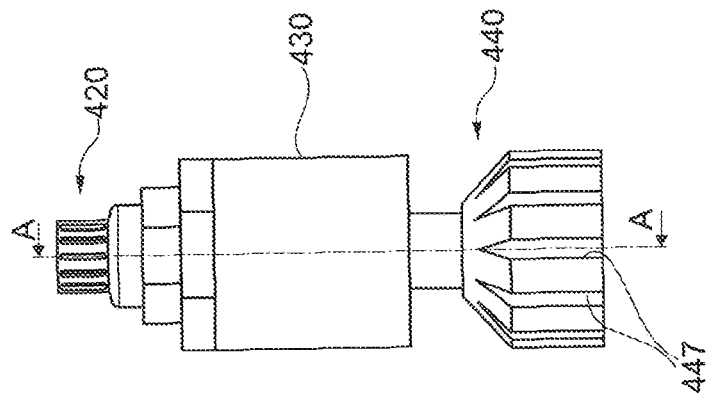
FIG. 13b is a side view of the FIG. 13a nozzle apparatus.
Figure 13C:
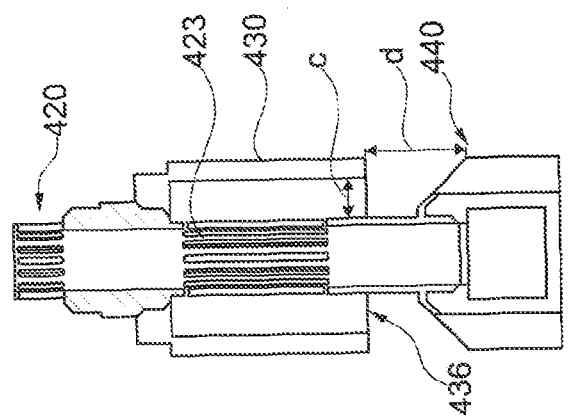
FIG. 13c is a sectional view through A-A of the FIG. 13b nozzle apparatus.
Figure 13A:
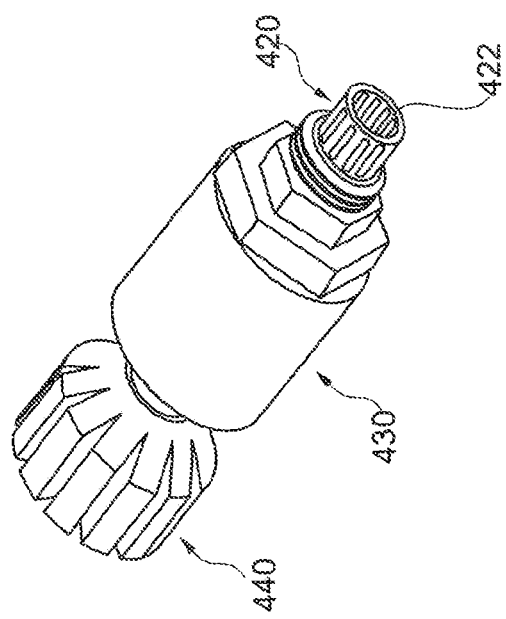
FIG. 13a is a perspective view of a further embodiment of a nozzle apparatus in accordance with the present invention.

A further embodiment of the invention is shown in FIGS. 13a-13c and similar parts use the corresponding reference numerals of earlier embodiments except preceded by a '4'. The FIG. 13a embodiment comprises an entry segregator 422, a main body 430 and a debris pot 440 which functions as described for earlier embodiments unless otherwise noted.

Notably an exit channel 436 is provided between the screen 423 and the housing 430, which is larger and directs fluid which has passed through the screen 423 towards the debris pot 440.

The debris pot 440 has a plurality of slots 447 on the outside perimeter thereof. Each slot 447 extends vertically (as orientated in use) and towards the centre of the debris pot 430 typically by 5-25 mm. Thus they are radially spaced from each other.

In use, relatively pure fluid is directed from the exit 436 onto the debris pot 430, which distributes the fluid into a pattern required in certain situations. The fluid will follow the path of the debris pot's 440 outer face design where it may flow through it and hit sections of it directing the flow in various directions. This will determine if the pattern is hollow cone or full cone pattern. The high velocity is normally full cone unless the housing 430 goes around the whole debris pot area (as per the FIG. 10 embodiment).

The distances 'c' and 'd' can be varied depending on the application requirements. For example d can be less than that shown in the figures and is typically 1-20 mm.

The velocity may be reduced by extending the length 'd' between the exit 436 and the debris pot 440. To reduce flow to reduce K-Factor or vice versa, the slots in the screen 423 may be less: 12 slots of 1 mm width over the same area rather than 24 slots of 1 mm for example. This would reduce the volume.

A further embodiment of the invention is shown in FIGS. 14*a*-14*c* and similar parts use the corresponding reference numerals of earlier embodiments except preceded by a '5'. The FIG. 14*a* embodiment comprises an entry segregator 522, a main body 530 and a debris pot 540 which functions as described for earlier embodiments unless otherwise noted.

In this embodiment the nozzle apparatus is orientated in an upwards direction during use and the pressure maintains the debris in the debris pot 540. The debris pot 540 has an angled flange 545 which is about 80 degrees to the housing 540.

In use, fluid proceeds through the entry segregator 522, through the main screen 523 and from between the housing 530 and the main screen 523 it is then directed by the angled portion 545 of the debris pot 540 to outside of the apparatus via an exit 536.

The nozzle apparatus shown in FIGS. 13*a-c* and 14*a-c* are often more suited to medium to high velocity applications, or medium to low velocity applications, compared to the nozzle apparatus of earlier embodiments which are more suited to high velocity applications. Nonetheless any embodiment herewith can be used for any velocity application.

Figure 15:
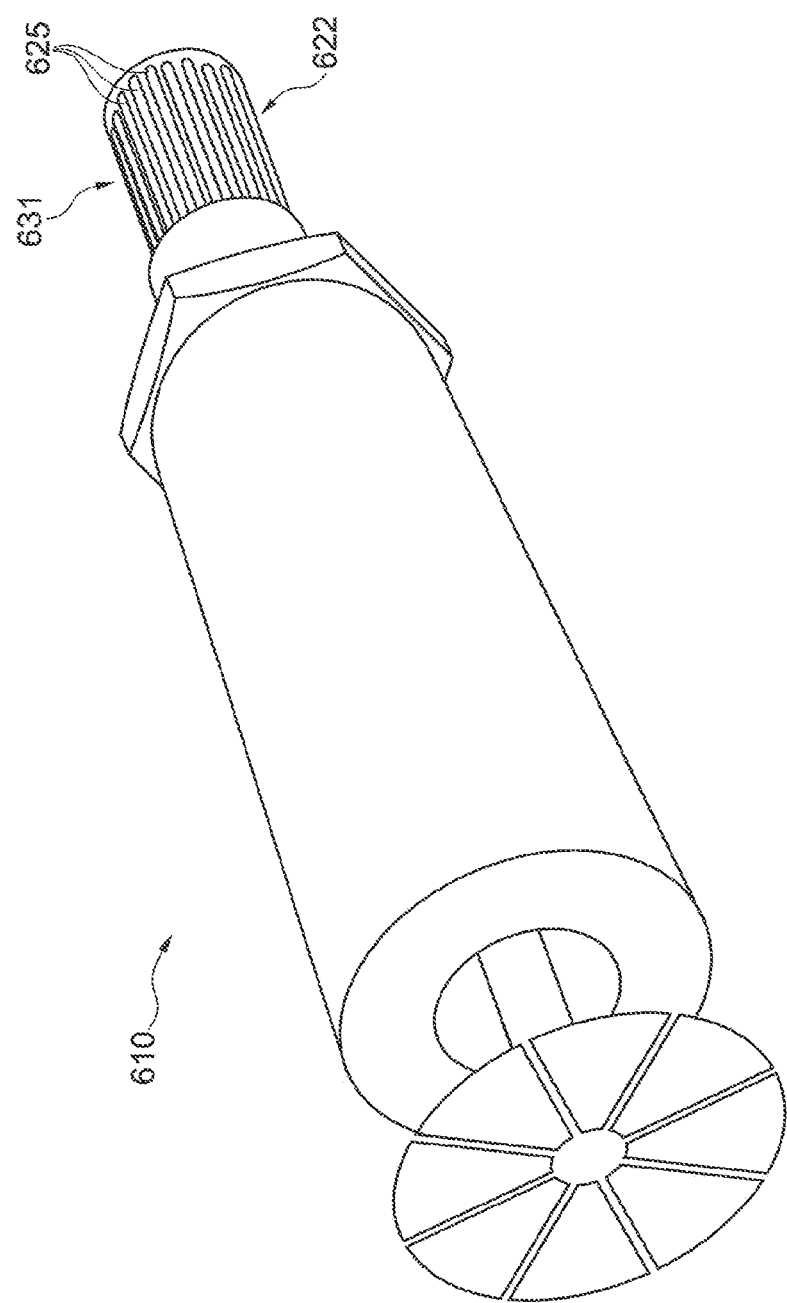
FIG. 15 is a perspective view of a yet further embodiment of a nozzle apparatus forming part of a nozzle system in accordance with the present invention.
Figure 16:
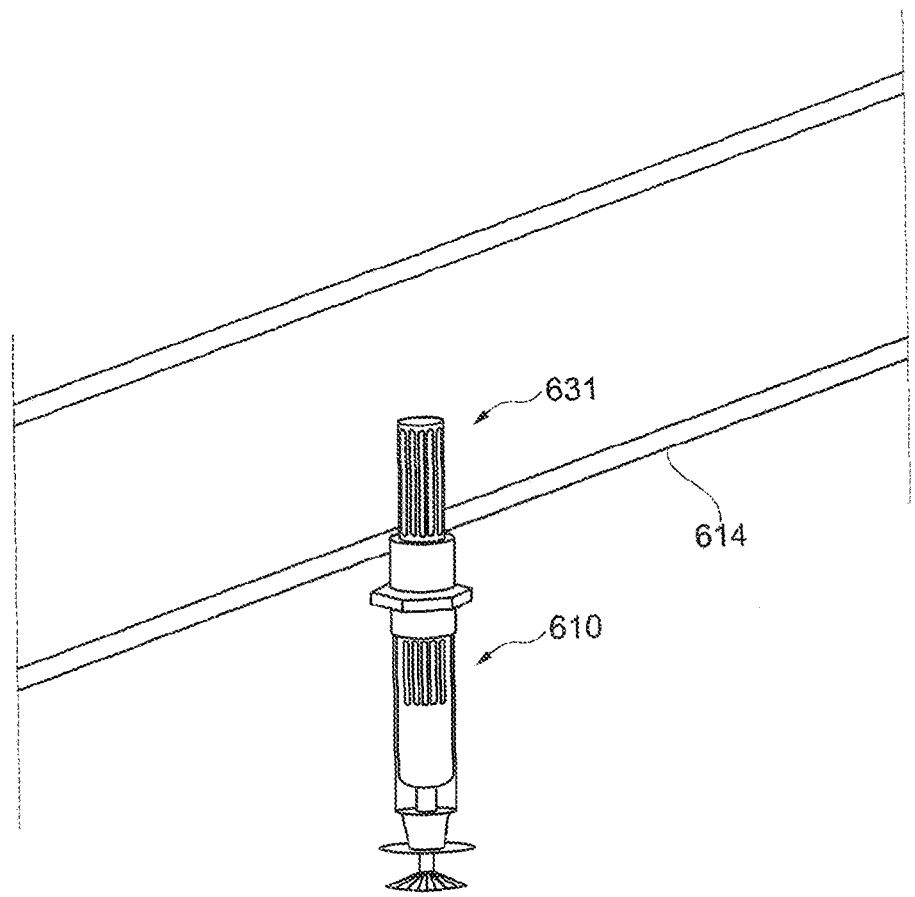
FIG. 16 is a perspective view of the FIG. 15 nozzle system comprising the nozzle apparatus and a pipeline.
Figure 17:
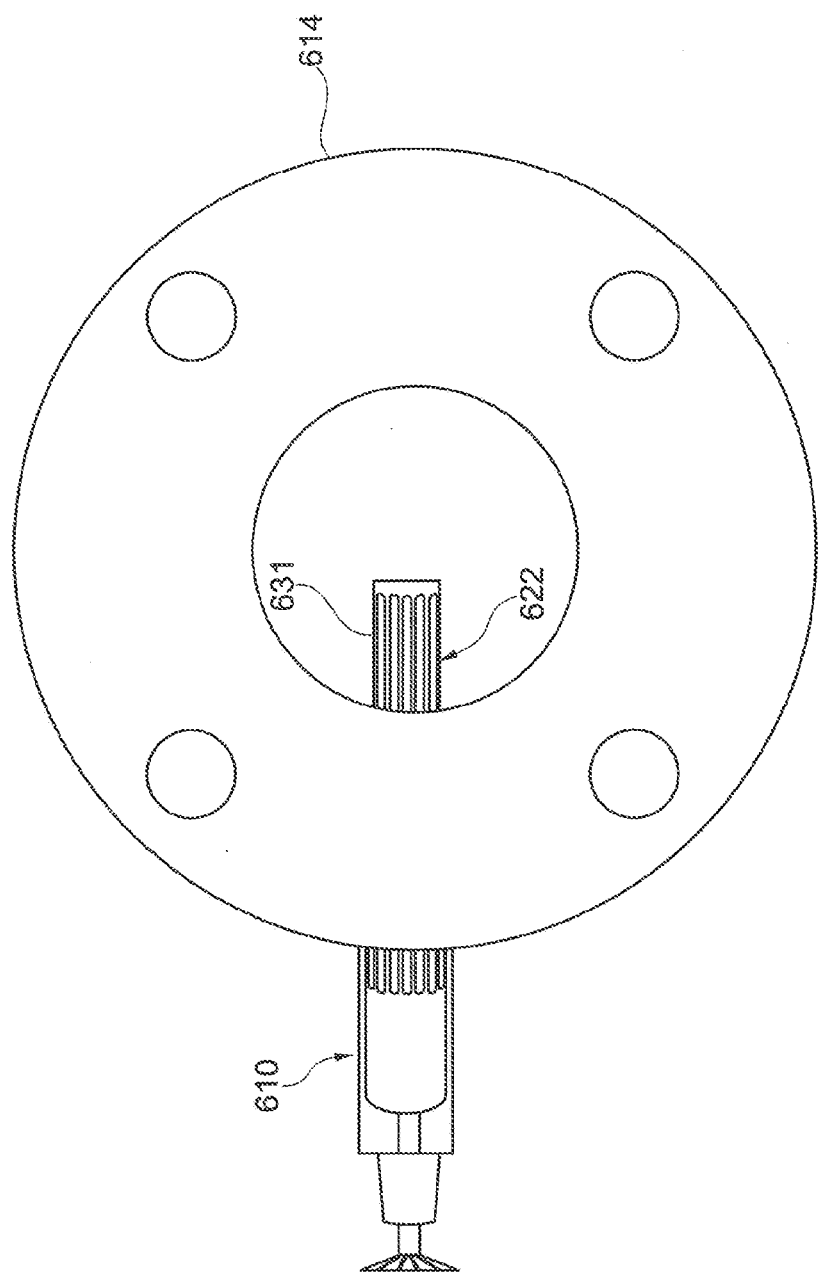
FIG. 17 is a plan view of the FIG. 15 embodiment of a nozzle system.

FIG. 15 shows a further embodiment of a nozzle apparatus 610 having an extended inlet 631. The inlet of this embodiment extends into a pipeline 614, as shown in FIGS. 16 and 17, such that the inlet extends in to the centre of the pipeline. In this way, even with debris built up on the inside of the pipeline 614, which would tend to block other nozzles, will not block so long as fluid is flowing through the centre of the pipeline 614. Such a configuration can be used with any of the nozzles disclosed herein. In this embodiment, the end of the inlet 631 is within 5 mm of the central axis of the pipeline 614 which has a diameter of 1" to 8".

The inlet 631 also has a secondary portion 622, which allows fluid to flow therein, and also comprises a series of liner slots 625 to filter the fluid.

Figure 18:
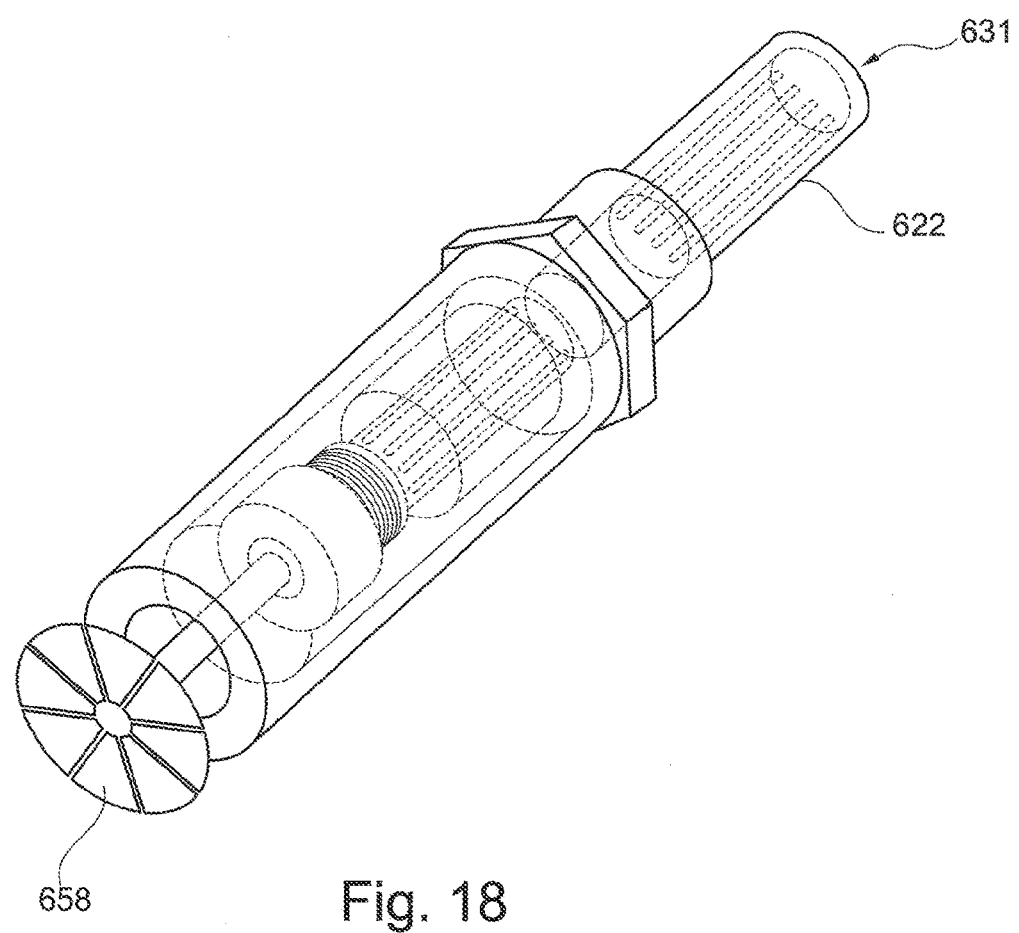
FIG. 18 is a further view of the FIG. 15 nozzle apparatus showing the internal components.

FIG. 18 shows the FIG. 15 nozzle apparatus with the outer housing removed, showing some internal components, which generally function as described for earlier embodiments.

Notably the inlet 631 is provided as a separate piece, and during assembly is placed into the pipeline. The remaining parts of the nozzle apparatus are then connected to the separate inlet piece 631.

The present embodiment also includes a dispersion plate 658 connected to the container by a cylindrical member.

Embodiments of the invention have a multi-purpose use being able to achieve K-Factor for sprinkler.

Embodiments of the invention are also safer in that less debris is distributed outwith the fluid. Such debris can cause injury to personnel e.g. it has been known to cut faces and has the potential to cause serious eye injuries.

Improvements and modifications may be made without departing from the scope of the invention.

The invention claimed is:

1. A nozzle apparatus comprising:
   an inlet,
   a nozzle outlet,
   a particulate filter disposed between the inlet and the nozzle outlet, the filter comprising a screen with at least one aperture therein;
   and a container;
   wherein the nozzle apparatus defines a first flow path between the filter and the container for particles too large for said filter and a second flow path towards the nozzle outlet for particles small enough for said filter;
   and wherein the container is provided downstream of the first flow path such that said first flow path terminates in the container and in use, particulate debris accumulates in the container;
   wherein an inlet flow path is defined between a portion of the nozzle apparatus between the inlet and the screen;
   and the inlet flow path and the first flow path, are co-linear.

2. A nozzle apparatus as claimed in claim 1, comprising a removable portion to allow access to the container.

3. A nozzle apparatus as claimed in claim 2, wherein the container comprises the removable portion.

4. A nozzle apparatus as claimed in claim 2, wherein the removable portion is removable by way of any one or more of a threaded connection, a snap fit connection, springs, clips and bolt & screw.

5. A nozzle apparatus as claimed in claim 2, wherein the removable portion is connected to, and separable from, the filter.

6. A nozzle apparatus as claimed in claim 1, wherein the first flow path terminates in the container.

7. A nozzle apparatus as claimed in claim 1, wherein the cross-sectional size of the inlet is at least the same size, optionally bigger, than the cross-sectional size of the first flow path.

8. A nozzle apparatus as claimed in claim 1, wherein the cross-sectional size of the inlet is at least the same size, optionally bigger, than the cross-sectional size of a flowpath between the filter and the container.

9. A nozzle apparatus as claimed in claim 1, wherein the filter comprises a screen comprising at least one aperture therein.

10. A nozzle apparatus as claimed in claim 9, wherein the at least one aperture of the screen is linear in shape.

11. A nozzle apparatus as claimed in claim 9, wherein the screen is a tubular screen with a passage therein, and said at least one aperture thereon is on a face of the tubular screen.

12. A nozzle apparatus as claimed in claim 9, wherein the size of the at least one aperture in the screen is equal to or smaller than the size of the nozzle outlet.

13. A nozzle apparatus as claimed in claim 1, wherein the portion of the nozzle apparatus between the inlet and the filter is a relatively central portion of the nozzle apparatus compared to the portion of the nozzle apparatus between the filter and the nozzle outlet.

14. A nozzle apparatus as claimed in claim 1, wherein the portion of the nozzle apparatus between the inlet and the filter and the first flow path are co-linear.

15. A nozzle apparatus as claimed in claim 1, wherein the nozzle outlet is a channel, disposed at an angle of from 10 to 50 degrees with respect to a main longitudinal axis of the filter.

16. A nozzle apparatus as claimed in claim 1, comprising an inlet screen comprising at least one first aperture sized to resist flow of particles of a pre-defined size and a second larger aperture sized to allow flow of particles of the pre-defined size.

17. The use of the apparatus as claimed in claim 1 with an oil based fluid, the use comprising flowing the oil based fluid through the inlet.

18. A nozzle apparatus comprising:
an inlet,
an outlet,
a filter disposed between the inlet and the outlet,
and a container;
wherein the nozzle apparatus defines a first flow path for particles too large for said filter and a second flow path towards the outlet for particles small enough for said filter;
wherein the container is provided downstream of the first flow path;
wherein the outlet is arranged such that, in use, fluid from the outlet is directed onto an outer face of the container; and
wherein the outer face of the container comprise a series of slots.

19. A nozzle apparatus comprising:
an inlet,
an outlet,
a filter disposed between the inlet and the outlet,
and a container;
wherein the nozzle apparatus defines a first flow path for particles too large for said filter and a second flow path towards the outlet for particles small enough for said filter;
wherein the container is provided downstream of the first flow path;
wherein an outer body is provided, which creates a third flow path between the filter and the outlet; and
wherein the outer body is a tube with an angled edge, said edge defining a portion of the outlet.

\* \* \* \* \*